US010384202B2

(12) United States Patent
Koh et al.

(10) Patent No.: US 10,384,202 B2
(45) Date of Patent: Aug. 20, 2019

(54) DEVICES, SYSTEMS, AND METHODS FOR DETECTING NUCLEIC ACIDS USING SEDIMENTATION

(71) Applicant: National Technology & Engineering Solutions of Sandia, LLC, Albuquerque, NM (US)

(72) Inventors: Chung-Yan Koh, Dublin, CA (US); Ulrich Y. Schaff, Livermore, CA (US); Gregory J. Sommer, Livermore, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 0 days.

(21) Appl. No.: 15/704,860

(22) Filed: Sep. 14, 2017

(65) Prior Publication Data

US 2018/0065118 A1 Mar. 8, 2018
US 2019/0210015 A9 Jul. 11, 2019

Related U.S. Application Data

(60) Division of application No. 13/423,008, filed on Mar. 16, 2012, now Pat. No. 9,795,961, which is a (Continued)

(51) Int. Cl.
*G01N 15/04* (2006.01)
*B01L 3/00* (2006.01)
(Continued)

(52) U.S. Cl.
CPC ............ *B01L 3/5027* (2013.01); *G01N 15/04* (2013.01); *G01N 15/042* (2013.01); *G01N 15/05* (2013.01);
(Continued)

(58) Field of Classification Search
None
See application file for complete search history.

(56) References Cited

U.S. PATENT DOCUMENTS 3,555,284 A 1/1971 Anderson
3,744,974 A 7/1973 Maddox
(Continued)

FOREIGN PATENT DOCUMENTS

WO WO-2008/143578 11/2008
WO WO-2009/098237 8/2009

OTHER PUBLICATIONS

U.S. Appl. No. 13/941,186, filed Jul. 12, 2013, Koh et al.
(Continued)

*Primary Examiner* — Rebecca L Martinez
(74) *Attorney, Agent, or Firm* — Helen S. Baca

(57) ABSTRACT

Embodiments of the present invention are directed toward devices, systems, and method for conducting nucleic acid purification and quantification using sedimentation. In one example, a method includes generating complexes which bind to a plurality of beads in a fluid sample, individual ones of the complexes comprising a nucleic acid molecule such as DNA or RNA and a labeling agent. The plurality of beads including the complexes may be transported through a density media, wherein the density media has a density lower than a density of the beads and higher than a density of the fluid sample, and wherein the transporting occurs, at least in part, by sedimentation. Signal may be detected from the labeling agents of the complexes.

18 Claims, 8 Drawing Sheets

Related U.S. Application Data continuation-in-part of application No. 12/891,977, filed on Sep. 28, 2010, now Pat. No. 8,945,914.

(60) Provisional application No. 61/362,398, filed on Jul. 8, 2010, provisional application No. 61/362,407, filed on Jul. 8, 2010.

(51) Int. Cl.
*G01N 33/543* (2006.01)
*G01N 15/05* (2006.01)
*G01N 15/00* (2006.01)

(52) U.S. Cl.
CPC . *G01N 33/54313* (2013.01); *G01N 33/54366* (2013.01); *B01L 3/50215* (2013.01); *B01L 3/502753* (2013.01); *B01L 2200/0668* (2013.01); *B01L 2200/0673* (2013.01); *B01L 2300/0803* (2013.01); *B01L 2400/0409* (2013.01); *G01N 2015/0065* (2013.01); *G01N 2015/045* (2013.01)

(56) References Cited

U.S. PATENT DOCUMENTS

| | | | |
|---|---|---|---|
| 4,125,375 A | 11/1978 | Hunter | |
| 4,156,570 A | 5/1979 | Wardlaw | |
| 4,554,071 A | 11/1985 | Ruijten et al. | |
| 4,656,143 A | 4/1987 | Baker et al. | |
| 4,683,579 A | 7/1987 | Wardlaw | |
| 4,844,818 A | 7/1989 | Smith | |
| 5,279,936 A | 1/1994 | Vorpahl | |
| 5,635,362 A | 6/1997 | Levine et al. | |
| 5,639,428 A | 6/1997 | Cottingham | |
| 5,705,628 A | 1/1998 | Hawkins | |
| 5,882,903 A | 3/1999 | Andrevski et al. | |
| 5,892,577 A | 4/1999 | Gordon | |
| 6,153,148 A | 11/2000 | Thomas | |
| 6,319,469 B1 | 11/2001 | Mian et al. | |
| 6,503,722 B1 | 1/2003 | Valkirs | |
| 6,887,384 B1 | 5/2005 | Frechet et al. | |
| 6,960,449 B2 | 11/2005 | Wang et al. | |
| 7,033,747 B2 | 4/2006 | Gordon et al. | |
| 7,157,049 B2 | 1/2007 | Valencia et al. | |
| 7,312,085 B2 | 12/2007 | Chou et al. | |
| 7,332,326 B1 | 2/2008 | Kellogg et al. | |
| 7,758,810 B2 | 7/2010 | Lee et al. | |
| 8,337,775 B2 | 12/2012 | Pugia et al. | |
| 8,945,914 B1 | 2/2015 | Schaff et al. | |
| 8,962,346 B2 | 2/2015 | Schaff et al. | |
| 9,186,668 B1 | 11/2015 | Schaff et al. | |
| 9,244,065 B1 | 1/2016 | Schaff et al. | |
| 9,304,128 B1 | 4/2016 | Koh et al. | |
| 9,304,129 B2 | 4/2016 | Schaff et al. | |
| 9,500,579 B1 | 11/2016 | Sommer et al. | |
| 9,702,871 B1 | 7/2017 | Koh et al. | |
| 2001/0055812 A1 | 12/2001 | Mian et al. | |
| 2002/0098535 A1 | 7/2002 | Wang et al. | |
| 2002/0106786 A1 | 8/2002 | Carvalho et al. | |
| 2002/0137068 A1 | 9/2002 | Haugland et al. | |
| 2002/0151043 A1 | 10/2002 | Gordon | |
| 2002/0153251 A1 | 10/2002 | Sassi et al. | |
| 2002/0164659 A1 | 11/2002 | Rao et al. | |
| 2002/0170825 A1 | 11/2002 | Lee et al. | |
| 2003/0013203 A1 | 1/2003 | Jedrzejewski et al. | |
| 2003/0124719 A1 | 7/2003 | Woodside | |
| 2003/0203504 A1 | 10/2003 | Hefti | |
| 2004/0072278 A1 | 4/2004 | Chou et al. | |
| 2005/0186685 A1 | 8/2005 | Kange et al. | |
| 2005/0215410 A1 | 9/2005 | Merino et al. | |
| 2005/0282220 A1 | 12/2005 | Prober et al. | |
| 2006/0171654 A1 | 8/2006 | Hawkins et al. | |
| 2008/0108047 A1 | 5/2008 | Woodside | |
| 2008/0149484 A1 | 6/2008 | Tolley et al. | |
| 2009/0004059 A1 | 1/2009 | Pugia et al. | |
| 2009/0069554 A1 | 3/2009 | Finne | |
| 2009/0209402 A1 | 8/2009 | Andersson | |
| 2009/0325186 A1 | 12/2009 | Hinnah et al. | |
| 2010/0068754 A1 | 3/2010 | Kirakossian | |
| 2010/0120596 A1 | 5/2010 | Froman et al. | |
| 2010/0151560 A1 | 6/2010 | Wo et al. | |
| 2011/0045958 A1 | 2/2011 | Pedrazzini | |
| 2013/0260447 A1 | 10/2013 | Link | |
| 2014/0273241 A1 | 9/2014 | Ochranek et al. | |
| 2015/0360225 A1 | 12/2015 | Schaff et al. | |
| 2016/0061829 A1 | 3/2016 | Schaff et al. | |
| 2016/0178619 A1 | 6/2016 | Koh et al. | |

OTHER PUBLICATIONS

U.S. Appl. No. 14/090,040, filed Nov. 26, 2013, Koh et al.
U.S. Appl. No. 14/957,405, filed Dec. 2, 2015, Koh.
U.S. Appl. No. 15/616,740, filed Jun. 7, 2017, Koh et al.
U.S. Appl. No. 15/669,426, filed Aug. 4, 2017, Phaneuf et al.
Abi-Samra et al., "Infrared controlled waxes for liquid handling and storage on a CD-microfluidic platform", Lab on a Chip, 2011, vol. 11, pp. 723-726.
Ahanotu et al., "Staphylococcal enterotoxin B as a biological weapon: recognition, management, and surveillance of Staphylococcal enterotoxin", Applied Biosafety, 2006, vol. 11 (3), pp. 120-126.
Albrecht et al., "Micro free-flow IEF enhanced active cooling and functionalized gels", Electrophoresis, 2006, vol. 27, pp. 4960-4969.
Amersham Biosciences AB, "Percoll: Methodology and Applications", Handbook No. 18-1115-69 (Ed. AC), 2001, Uppsala, Sweden, pp. 1-84.
Amukele et al., "Ricin A-chain activity on stem-loop and unstructured DNA substrates", Biochemistry, 2005, vol. 44(11), pp. 4416-4425.
Andersson et al., "Parallel nanoliter microfluidic analysis system", Analytical Chemistry, 2007, vol. 79(11), pp. 4022-4030.
Baldwin, "How Hofmeister ion interactions affect protein stability", Biophysical Journal, 1996, vol. 71, pp. 2056-2063.
Berlier et al., "Quantitative comparison of long-wavelength Alexa Fluor dyes to Cy dyes: fluorescence of the dyes and their bioconjugates", Journal of Histochemistry and Cytochemistry, 2003, vol. 51(12), pp. 1699-1712.
Berry et al., "One-step purification of nucleic acid for gene expression analysis via immiscible filtration assisted by surface tension", Lab on a Chip, 2011, vol. 11(10), pp. 1747-1753.
Boyko et al., "Cell-free DNA—a marker to predict ischemic brain damage in a rat stroke experimental model", Journal of Neurosurgery and Anesthesiology, 2011, vol. 23(3), pp. 222-228.
Brigotti et al., "Shiga toxin 1 acting on DNA in vitro is a heat-stable enzyme not requiring proteolytic activation", Biochimie Journal, 2004, vol. 86(45), pp. 305-309.
Buck et al., "Design strategies and performance of custom DNA sequencing primers", Biotechniques, 1999, vol. 27(3), pp. 528-536.
Carbera et al., "Formation of natural pH gradients in a microfluidic device under flow conditions: model and experimental validation", Analytical Chemistry, 2001, vol. 73(3), pp. 658-666.
Carney, "Rapid diagnostic tests employing latex particles", Analytical Proceedings, 1990, vol. 27, pp. 99-100.
Churchill et al., "Detection of Listeria monocytogenes and the toxin listeriolysin O in food", Journal of Microbiological Methods, 2006, vol. 64(2), pp. 141-170.
Cui et al., "Multistage isoelectric focusing in a polymeric microfluidic chip", Analytical Chemistry, 2005, vol. 77(24), pp. 7878-7886.
Curtis et al., "A molecular approach to bioseparations: protein-protein and protein-salt interactions", Chemical Engineering Science, 2006, vol. 61, pp. 907-923.
Czeiger et al., "Measurement of circulating cell-free DNA levels by a new simple fluorescent test in patients with primary colorectal cancer", American Journal of Clinical Pathology, 2011, vol. 135(2), pp. 264-270.
Das et al., "Effects of separation length and voltage on isoelectric focusing in a plastic microfluidic device", Electrophoresis, 2006, vol. 27(18), pp. 3619-3626.

(56) References Cited

OTHER PUBLICATIONS

Endo et al., "RNA N-glycosidase activity of ricin A-chain. Mechanism of action of the toxic lectin ricin on eukaryotic ribosomes", The Journal of Biological Chemistry, 1987, vol. 262(17), pp. 8128-8130.

Fologea et al, "Detecting single stranded DNA with a solid state nanopore", Nano Letters, 2005, vol. 5(10), pp. 1905-1909.

Glorikian et al., "Microfluidics for IVDS—Smart consumable product development: implications for molecular diagnostics", DX Directions 2010, Spring, pp. 12-16.

Goldshtein et al., "A rapid direct fluorescent assay for cell-free DNA quantification in biological fluids", Annals of Clinical Biochemistry, 2009, vol. 46(Pt 6), pp. 488-494.

Görg et al., "Recent developments in two-dimensional gel electrophoresis with immobilized pH gradients: wide pH gradients up to pH 12, longer separation distances and simplified procedures", Electrophoresis, 1999, vol. 20(4-5), pp. 712-717.

Görg et al., "The current state of two-dimensional electrophoresis with immobilized pH gradients", Electrophoresis, 2000, vol. 21(6), pp. 1037-1053.

Gorkin et al., "Centrifugal microfluidics for biomedical applications", Lab on a Chip, 2010, vol. 10, pp. 1758-1773.

Gusev et al., "Capillar columns with in situ formed porous monolithic packing for micro high-performance liquid chromatography and capillary electrochromatography", Journal of Chromatography A, 1999, vol. 855(1), pp. 273-290.

Hatch et al., "Integrated preconcentration SDS-PAGE of proteins in microchips using photopatterned cross-linked polyacrylamide gels", Analytical Chemistry, 2006, vol. 78(14), pp. 4976-4984.

Herr et al., "Microfluidic immunoassays as rapid saliva-based clinical diagnostics", Proceedings of the National Academy of Science USA, 2007, vol. 104(13), pp. 5268-5273.

Herr et al., "On-chip coupling of isoelectric focusing and free solution electrophoresis for multidimensional separations", Analytical Chemistry, 2003, vol. 75(5), pp. 1180-1187.

Holmberg et al., "Depurination of A4256 in 28 S rRNA by the ribosome-inactivating proteins from barley and ricin results in different ribosome conformations", Journal of Molecular Biology, 1996, vol. 259(1), pp. 81-94.

Holmes et al., "Leukocyte analysis and differentiation using high speed microfluidic single cell impedance cytometry", Lab on a Chip, 2009, vol. 9, pp. 2881-2889.

Huang et al., "The primary structure of Staphylococcal enterotoxin B: III, The cyanogen bromide peptides of reduced and aminoethylated enterotoxin B, and the complete amino acid sequence", Journal of Biological Chemistry, 1970, vol. 245(14), pp. 3518-3525.

Huang et al., "Microfabrication of a tapered channel for isoelectric focusing with thermally generated pH gradient," Electrophoresis, 2002, vol. 23(20), pp. 3504-3510.

IVD Technology, "Microfluidic applicatons for IVDs", DX Directions, 2010, Spring, pp. 1-26.

Invitrogen Life Technologies, "ZOOM IEF Fractionator, Instructional Manual", Catalog Nos. ZF10001 & ZF10002, Version C, Jul. 2004 (64 pp.).

Kim et al., "Fully integrated lab-on-a-disc for nucleic acid analysis of food-borne pathogens", Analytical Chemistry, 2014, vol. 86, pp. 3841-3848.

Koh et al., "Centrifugal microfluidic platform for ultrasensitive detection of botulinum toxin", Analytical Chemistry, 2015, vol. 81, pp. 922-928.

Lee et al., "Fully integrated lab-on-a-disc for simultaneous analysis of biochemistry and immunoassay from whole blood", Lab on a Chip, 2011, vol. 11(1), pp. 70-78.

Lee et al., "A fully automated immunoassay from whole blood on a disc", Lab on a Chip, 2009, vol. 9(11), pp. 1548-1555.

Lim et al., "Bead-based microfluidic immunoassays: The next generation", Biosensors and Bioelectronics, 2007, vol. 22(7), pp. 1197-1204.

Lim et al., "Rapid isoelectric trapping in a micropreparative-scale multicompartment electrolyzer", Electrophoresis, 2007, vol. 28(12), pp. 1851-1859.

Lo et al., "Photopolymerized diffusion-defined polyacrylamide gradient gels for on-chip protein sizing", Lab on a Chip, 2008, vol. 8(8), pp. 1273-1279.

Lo et al., "Plasma DNA as a prognostic marker in trauma patients", Clinical Chemistry, 2000, vol. 46(3), pp. 319-323.

Long et al., "Integration of nanoporous membranes for sample filtration/preconcentration in microchip electrophoresis", Electrophoresis, 2006, vol. 27(24), pp. 4927-4934.

Madou et al., "Lab on a CD", Annual Review of Biomedical Engineering, 2006, vol. 8, pp. 601-628.

Maes et al., "Comparison of sample fixation and the use of LDS-751 or anti-CD45 or leukocyte identification in mouse whole blood for flow cytometry", Journal of Immunological Methods, 2007, vol. 319(1-2), pp. 79-86.

McBain et al., "Polyethyleneimine functionalized iron oxide nanoparticles as agents for DNA delivery and transfection", Journal of Material Chemistry, 2007, vol. 17(24), pp. 2561-2565.

Melting Temperature Calculation. Retrieved on asf from the internet: http://www.biophp.org/minitools/melting_temperature/demo.php?primer=CGT+TAC+CCG+CAG&basic-1&NearestNeighbor=1&cp=200&cs=50&cmg=0.

Min et al., "Functional integration of DNA purification and concentration into a real time micro-PCR chip", Lab on a Chip, 2011, vol. 11(2), pp. 259-265.

O'Farrell, "High resolution two-dimensional electrophoresis of proteins", Journal of Biological Chemistry, 1975, vol. 250(10), pp. 4007-4021.

Ogle et al., "Preparative-scale isoelectric trapping separations using a modified Gradiflow unit", Journal of Chromatography A, 2002, vol. 979(1-2), pp. 155-161.

Price et al., "Light-scattering immunoassay", in Principles and Practice Immunoassay (Second Ed., C.P. Price & D.J. Newman, eds.), 1997, Stockton Press (New York, NY), Chap. 18, pp. 445-480.

PubChem Search results for "2,3-dihydroxypropyl octanoate," retrieved on Oct. 5, 2016 from https://www.ncbi.nlm.nih.gov/pcompound/?term=2%2C3-dihydroxypropyl+octanoate (4 pp.).

PubChem Entry for "TWEEN 20," retrieved on Oct. 4, 2016 from https://pubchem.ncbi.nlm.nih.gov/compound/Tween_20#section=Names-and-identifiers (2 pp.).

Rhodes et al., "Plasma DNA concentration as a predictor of mortality and sepsis in critically ill patients", Critical Care, 2006, vol. 10(2), Article R60 (pp. 1-7).

Riahi et al., "Molecular detection of bacterial pathogens using microparticle enhanced double-stranded DNA probes", Analytical Chemisty, 2011, vol. 83(16), pp. 6349-6354 and Supporting Information (8 pp.).

Rider et al., "A B cell-based sensor for rapid identification of pathogens", Science, 2003, vol. 301, pp. 213-215.

Riegger et al., "Read-out concepts for multiplexed bead-based fluorescence immunoassays on centrifugal microfluidic platforms", Sensors and Actuators A—Physical, 2006, vol. 126, pp. 455-462.

Righetti PG, "The Alpher, Bethe, Gamow of isoelectric focusing, the alpha-Centaury of electrokinetic methodologies—part I", Electrophoresis, 2006, vol. 27(5-6), pp. 923-938.

Righetti, "The Alpher, Bethe and Gamow of IEF, the alpha-Centaury of electrokinetic methodologies—part II: immobilized pH gradients", Electrophoresis, 2007, vol. 28(4), pp. 545-555.

Saukkonen et al., "Cell-free plasma DNA as a predictor of outcome in severe sepsis and septic shock", Clinical Chemistry, 2008, vol. 54(6), pp. 1000-1007.

Schaff et al., "Whole blood immunoassay based on centrifugal bead sedimentation", Clinical Chemistry, 2011, vol. 57(5), pp. 753-761.

Schembri et al., "Portable simultaneous multiple analyte whole-blood analyzer for point-of-care testing", Clinical Chemistry, 1992, vol. 38(9), pp. 1665-1670.

Schneider et al., "Characterization of EBV-genome negative "null" and "t" cell lines derived from children with acute lymphoblastic leukemia and leukemic transformed non-Hodgkin lymphoma", International Journal of Cancer, 1977, vol. 19(5), pp. 621-626.

(56) References Cited

OTHER PUBLICATIONS

Sigma-Aldrich product page For TWEEN 20, archived from Jun. 28, 2012, retrieved on Oct. 5, 2016 from https://web.archive.org/web/20120628080753/http://www.sigmaaldrich.com/catalog.product/sial/p1379?ang=en&region= (43 pp.).

Sommer et al., "On-chip isoelectric focusing using photopolymerized immobilized pH gradients", Analytical Chemistry, 2008, vol. 80(9), pp. 3327-3333.

Suzuki et al., "Experimental optimization of probe length to increase the sequence specificity of high-density oligonucleotide microarrays", BMC Genomics, 2007, vol. 8, Art. 373 (13 pp.).

Tan et al., "Miniaturized capillary isoelectric focusing in plastic microfluidic devices", Electrophoresis, 2002, vol. 23(20), pp. 3638-3645.

Yu et al., "Bioinformatic processing to identify single nucleotide polymorphism that potentially affect Ape1 function", Mutation Research/Genetic Toxicology and Environmental Mutagenesis, 2011, vol. 722(2), pp. 140-146.

Zhang et al., "A new biodosimetric method: branched DNA-based quantitative detection of B1 DNA in mouse plasma", British Journal of Radiology, 2010, vol. 83, pp. 694-701.

Ziegler et al., "Circulating DNA: a new diagnostic gold mine?", Cancer Treatment Reviews, 2002, vol. 28, pp. 255-271.

Zilberstein et al., "Parallel isoelectric focusing chip", Proteomics, 2004, vol. 4(9), pp. 2533-2540.

Zilberstein et al., "Parallel isoelectric focusing II", Electrophoresis, 2004, vol. 25(21-22), pp. 3643-3651.

Zilberstein et al., "Parallel processing in the isoelectric focusing chip", Electrophoresis, 2003, vol. 24(21), pp. 3735-3744.

Zuo et al., "A method for global analysis of complex proteomes using sample prefractionation by solution isoelectrofocusing prior to two-dimensional electrophoresis", Analytical Biochemistry, 2000, vol. 284(2), pp. 266-278.

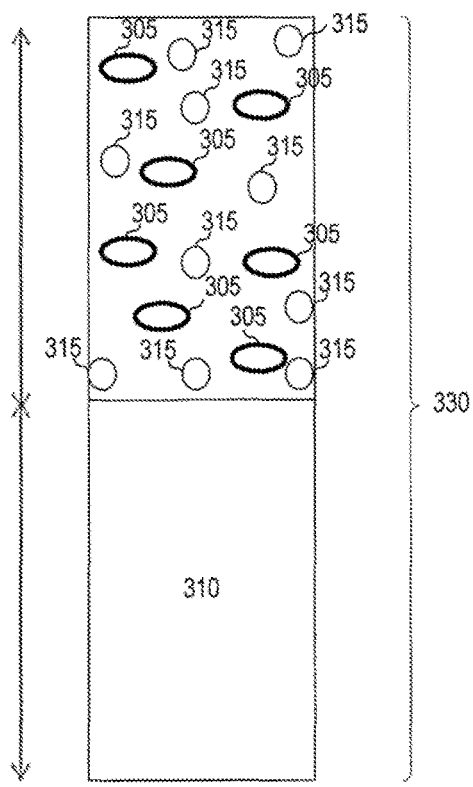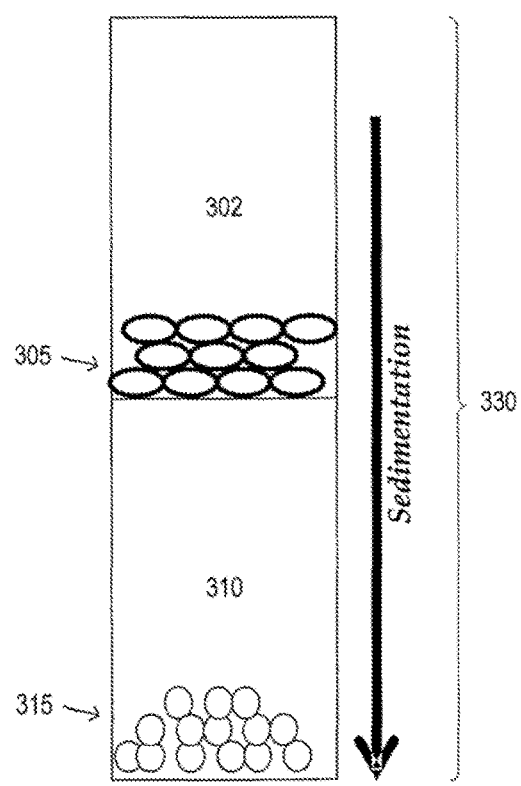
*Before Sedimentation*  *After Sedimentation*
Figure 3A  Figure 3B

DEVICES, SYSTEMS, AND METHODS FOR DETECTING NUCLEIC ACIDS USING SEDIMENTATION

CROSS-REFERENCE TO RELATED APPLICATION(S)

This application is a divisional of U.S. application Ser. No. 13/423,008, filed Mar. 16, 2012, which in turn is a continuation-in-part of U.S. application Ser. No. 12/891,977, filed Sep. 28, 2010, entitled "Devices, systems, and methods for conducting sandwich assays using sedimentation," which application claims the benefit of the earlier filing dates of U.S. Provisional Applications 61/362,398 filed Jul. 8, 2010 and 61/362,407 filed Jul. 8, 2010. All afore-mentioned applications are hereby incorporated by reference, in their entirety, for any purpose.

STATEMENT REGARDING RESEARCH & DEVELOPMENT

Described examples were made with Government support under Contract No. DE-NA0003525 awarded by the United States Department of Energy/National Nuclear Security Administration. The Government has certain rights in the invention, including a paid-up license and the right, in limited circumstances, to require the owner of any patent issuing in this invention to license others on reasonable terms.

TECHNICAL FIELD

Embodiments of the invention relate generally to assay systems and examples include methods, systems, and apparatus employing sedimentation forces for conducting assays, including the detection and/or quantification of cell-free DNA or other nucleic acids.

BACKGROUND

Elevated presence of cell-free DNA (CFD) in blood has been linked to cancers, sepsis, radiation poisoning, brain damage, and stroke. The use of CFD as a biomarker for diagnosing such conditions has been inhibited by the complexity and expense of current methods for determining the concentration. Methods for determining CFD concentration in biological samples such as serum include labeling with DNA responsive fluorescent dyes such as PicoGreen® from Life Technologies. Although capable of measuring DNA directly in serum, such methods suffer from high background noise signal and reduced sensitivity due to the presence of serum which exhibits substantial and variable autofluorescence. Moreover, spectroscopic determination of DNA concentration may typically be performed using UV absorbance, however, serum components also absorb at the relevant wavelengths, which complicates the analysis. Alternative high sensitivity methods for measuring CFD typically involve labor- and time-intensive steps including DNA extraction and purification followed by gel electrophoresis and/or quantitative real-time polymerase chain reaction (qPCR).

Microfluidic systems, including "lab on a chip" or "lab on a disk" systems continue to be in development. See, Lee, B. S., et. al., "A fully automated immunoassay from whole blood on a disc," Lab Chip 9, 1548-1555 (2009) and Madou, M. et. al., "Lab on a CD," Annu. Rev. Biomed. Engr. 8, 601-628 (2006), which articles are hereby incorporated by reference in their entirety for any purpose.

BRIEF DESCRIPTION OF THE DRAWINGS

FIG. 3A-3B is a schematic illustration of a detection region of a fluid-holding device before (FIG. 3A) and after (FIG. 3B) sedimentation in accordance with an embodiment of the present invention.

DETAILED DESCRIPTION

Certain details are set forth below to provide a sufficient understanding of embodiments of the invention. However, it will be clear to one skilled in the art that embodiments of the invention may be practiced without various of these particular details. In some instances, well-known chemical structures, chemical components, molecules, materials, electronic components, circuits, control signals, timing protocols, and software operations have not been shown in detail in order to avoid unnecessarily obscuring the described embodiments of the invention.

Embodiments of the present invention are directed toward systems, apparatus, and methods for detecting and/or quantifying cell-free DNA or other nucleic acids in a sample. As mentioned above, existing methods for detecting cell-free DNA in complex biological samples may be cumbersome or suffer limited sensitivity. Examples according to the current invention include analysis of target analytes including DNA, RNA, or other compositions of single or double stranded nucleic acids. References will be made herein to and examples given of applications targeting DNA, but it should be understood that in other examples, RNA or other compositions of single or double stranded nucleic acids may be targeted for detection and/or quantification.

Co-pending U.S. application Ser. No. 12/891,977, filed Sep. 28, 2010, entitled "Devices, systems, and methods for conducting sandwich assays using sedimentation," is hereby incorporated by reference in its entirety for any purpose. The aforementioned application includes examples of the formation of complexes including a capture agent, target analyte, and labeling agent on sedimentation particles. Thus, target agents may be separated from sample by affinity with a capture agent, and the sedimentation particles passed through a density medium. Examples of the present invention may capture nucleic acids directly to a surface of a sedimentation particle using the unique charge and chemical characteristics of nucleic acids. Accordingly, complexes formed on the sedimentation particle may simply include a target analyte (e.g. nucleic acid) and labeling agent. This separation mechanism may advantageously provide simple mechanisms for nucleic acid purification and measurement.

Figure 1:
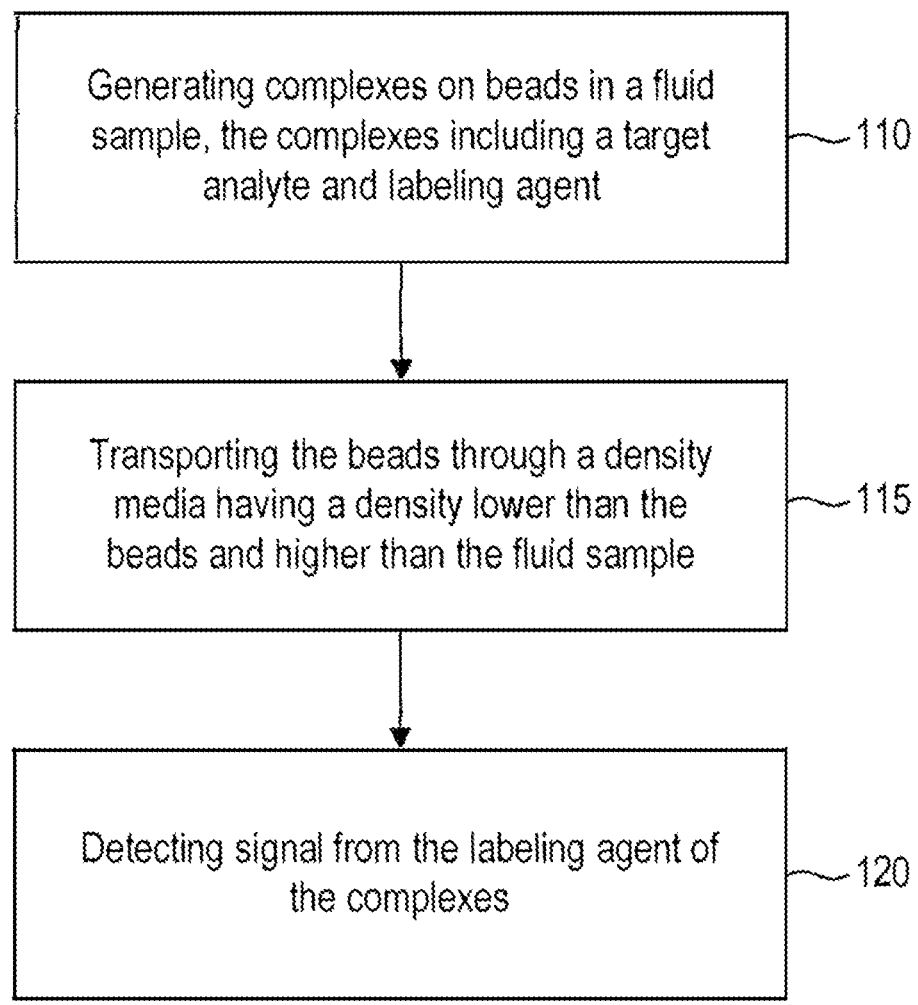
FIG. 1 is a flowchart illustrating a method for conducting a nucleic acid assay in accordance with embodiments of the present invention.

FIG. 1 is a flowchart illustrating a method for conducting a nucleic acid assay in accordance with embodiments of the present invention. In block 110, complexes may be generated on sedimentation particles (e.g. beads) in a fluid sample. The complexes may include a target analyte (e.g. cell-free DNA) and labeling agent. Block 110 may be followed by block 115. In block 115, the sedimentation particles may be transported through a density media having a density lower than the beads but higher than the fluid sample. Gravitational forces, generated naturally or by centrifugation, may be used to transport the beads through the density media. The sedimentation particles accordingly may sediment out of the fluid sample, forming a concentrated pellet. Block 115 may be followed by block 120. In block 120, signal may be detected from the labeling agent of the complexes. In some examples, by separating the sedimentation particles from the sample fluid using gravitational forces, the beads are also concentrated, which may eliminate or reduce a need for amplification of the labeling agent.

In block 110, complexes including the target analyte (e.g. cell-free DNA), and labeling agent may be formed on beads in a fluid sample. Any sedimentation particles with appropriate surface properties, including beads, may be used, including but not limited to, polystyrene beads or silica beads. Substantially any bead radii may be used. Examples of beads may include beads having a radius ranging from 150 nanometers to 10 microns.

In nucleotide quantification sedimentation assays, the beads may have surface modifications to enhance nucleotide capture. Similarly, the labeling agent may be any suitable labeling agent for binding to the target nucleotide and providing a detection signal. Examples include chemical dyes with high binding affinity for DNA and/or other nucleic acids (e.g. nucleic acid dyes). Fluorescent labels including the aforementioned chemical dyes may provide an optical detection signal, however colorimetric or radioactive tags may also be used.

In examples of nucleic acid (e.g. cell-free DNA) assays, the sedimentation particles may be implemented as silica microparticles. The sedimentation particles used in nucleic acid assays may advantageously have a positively-charged surface. For example, the surfaces of the sedimentation particles (e.g. beads) may be amine-modified. In one example, 1 μm silica microparticles are used. In examples of cell-free DNA assays, the complexes may be attached to the sedimentation particles (e.g. beads, silica microparticles) due to interaction between the positively charged particle surface and negatively-charged nucleic acid.

In examples of nucleic acid assays, the sample may include (either originally or after mixing) a buffer in which nucleic acids may remain negatively charged while proteins may generally maintain a net neutral or positive charge. For example, a high salt and low pH binding buffer may be used (e.g. 1M sodium sulfate and 1M sodium acetate, pH 3). In some examples, the fluid sample may be configured to have an acidic pH (e.g. less than 4, less than 3.5, less than 3 in some examples). The acidic fluid may advantageously cause proteins or other potentially contaminating components to have a positive charge while nucleic acids may maintain a negative charge. Generally, the buffer may include salts (e.g. kosmotropes, or order-forming salts) such that the nucleic acids bind to the silica surfaces of the sedimentation particles (e.g. beads). By ordering water and thus increasing the hydrophobic effect, kosmotropes may facilitate protein aggregation to the exclusion of other molecules such as nucleic acids, further decreasing the likelihood of assay interference by proteins. In other examples, other binding buffers including, but not limited to chaotropic salts or PBS, may be used to bind the nucleic acids (e.g. DNA) to a negatively charged silica surface.

In some examples, a negatively charged bead surface may be obtained, for example, through use of untreated silica particles (e.g. microparticles as formed by standard manufacturing practices prior to functionalization), silica particles treated with strong acids, through functionalization of the silica surface with negatively charged moieties (e.g. carboxylic acids, phosphates), or through the use of polymeric microparticles with negatively charged surface moieties (e.g. carboxylic acid functionalized polystyrene microparticles). In the case of chaotropic salts (e.g. guanidine hydrochloride, potassium thiocyanate), the interaction may not be a direct binding to the surface of the bead such as the case of kosmotropic salts but rather an indirect binding. For example, and without being bound by theory, the positive ion of a chaotropic salt may allow interaction between the surface of the negatively charged bead and the negatively charged nucleic acid by forming a salt bridge (e.g. the positive ion may mediate the interaction with the surface of the bead and the nucleic acid thus preventing repulsion due to like-charge interactions). Additionally, chaotropic salts may disrupt the order of water molecules surrounding nucleic acids, reducing hydrogen bonding and permitting a greater number of salt bridge formations. Other combinations or silica surface charge and binding buffer are possible and known to the art. When chaotropic salts or PBS are used, the background may be higher and mean fluorescence intensity of the signal may be lower, however.

In examples of nucleic acid (e.g. cell-free DNA) assays, the labeling agent may be implemented as a dye for staining the nucleic acids. Dyes that bind to DNA or other target nucleic acids (e.g. nucleic acid dyes) with high affinity (e.g. binding constant <20 nM) are highly preferred. Conventional DNA dyes that bind more weakly to DNA may be removed from beads during sedimentation, weakening observed signal. Suitable dyes include, but are not limited to, ethidium homodimer 1, ethidium homodimer 2, and SYBR® gold. The aforementioned dyes may exhibit large increases in quantum yield upon binding to the nucleic acids (e.g. DNA), which may improve detection.

Figures 2A, 2B, 2C, 2D:
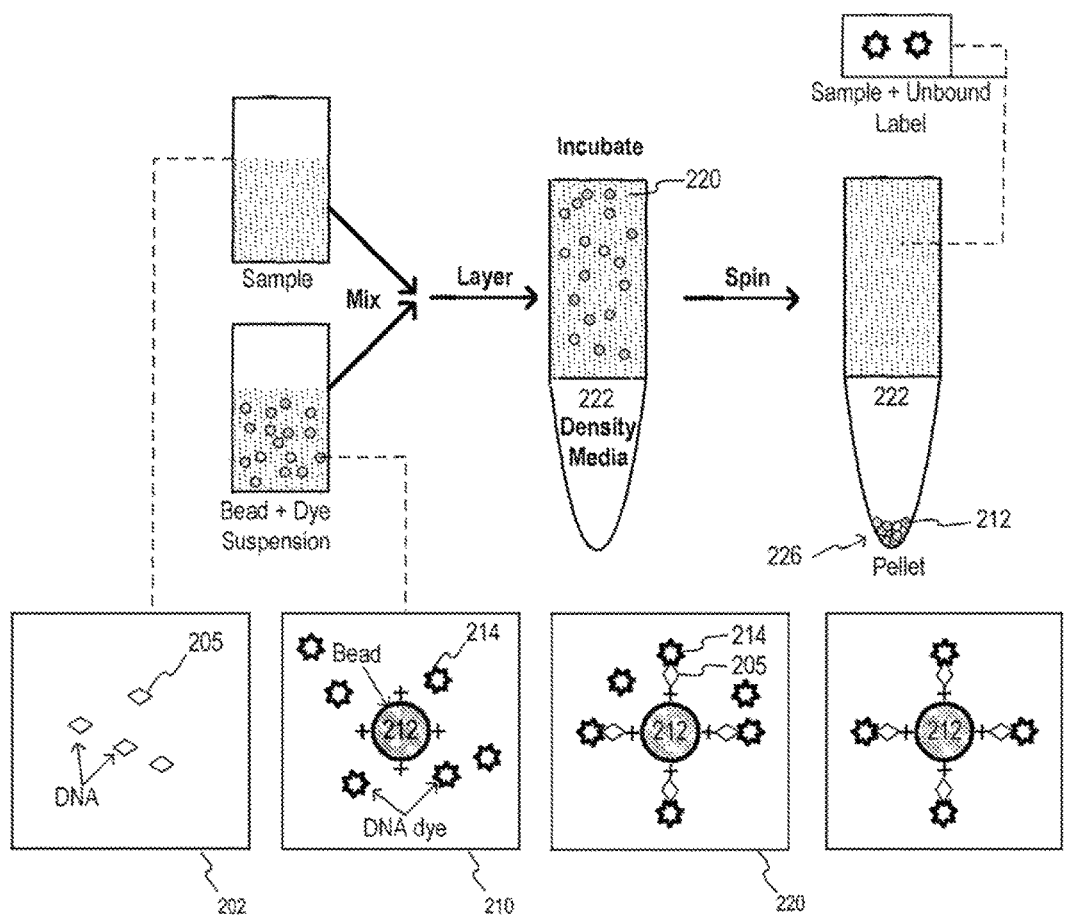
FIGS. 2A-2D are schematic illustrations of a DNA assay in accordance with embodiments of the present invention.

FIGS. 2A-2D are schematic illustrations of a DNA assay in accordance with embodiments of the present invention. Although a DNA assay is shown, as mentioned above, any nucleic acids may be detected and/or quantified in other examples. In FIG. 2A, a sample 202 is shown including DNA, e.g. DNA 205. Samples used in DNA assays may or may not include DNA, as the assay may be used to detect the presence of DNA and/or to quantify the amount of DNA present in a sample. As described above, the sample may include any of a variety of fluids, including biological fluids such as serum.

FIG. 2B is a schematic illustration of a suspension of sedimentation particles in accordance to an embodiment of the present invention. In FIG. 2B, a particle suspension 210 may include sedimentation particles (e.g. bead 212) and labeling agents (e.g. dye 214). As has been described above, the sedimentation particles may have a positive charge (e.g. amine-treated silica particles). In other examples, the sedimentation particles may have a negative charge. The dye may be configured to stain DNA or other nucleic acids. As shown in FIG. 2A-2D, the sample and the particle suspension may be mixed (e.g. by vortexing, pipetting, and/or sonication). Either the sample, the particle suspension, or both, may contain salts as described above such that the DNA, if present in the mixture, may have a negative charge while proteins that may be present in the sample may have a positive or neutral charge. In other examples, salts may be present to facilitate negatively-charged nucleic acids forming complexes with beads having a negatively-charged surface. Such binding may make use of salt bridges, as discussed above.

FIG. 2C is a schematic illustration of complexes that may be formed in the mixture. DNA 205 may be labeled with the dye 214 and form a complex with the positively-charged bead 212. Any number of complexes may be formed on the bead, with four shown in FIG. 2C. The mixture 220 may be layered over a density medium 222. The density media 222 is generally a liquid which may have a density lower than a density of sedimentation particles (e.g. beads) used in an assay and higher than a density of the fluid sample. The density media may generally be implemented using a fluid having a density selected to be in the appropriate range—lower than a density of the beads used to conduct an assay and higher than a density of the fluid sample. In some examples, a fluid sample may be diluted for use with a particular density media. The density media may include, for example, a salt solution containing a suspension of silica particles which may be coated with a biocompatible coating. An example of a suitable density media is Percoll™, available from GE Lifesciences. Particular densities may be achieved by adjusting a percentage of Percoll™ in the salt solution. More generally, viscosity and density may be adjusted by changing a composition of the media. Varying the concentration of solutes such as, but not limited to, sucrose or dextran, in the density media, may adjust the density and/or viscosity of the media. The mixture 220 may be introduced into a fluidic feature (e.g. microfluidic device, including those described herein, vial, or other fluid-containing structure) such that the mixture 220 is next to or on top of the density media 222. Before or after the layering, the mixture may be incubated to allow for formation of the complexes. The density media may have a density that is greater than the sample but less dense than the sedimentation particles (e.g. bead 212). Sedimentation forces (e.g. centrifugal or gravitational) may be applied to the mixture. For example, the feature containing the mixture may be spun to apply a centrifugal force.

FIG. 2D is a schematic illustration of the fluid containing structure following sedimentation. The sedimentation particles, including the bead 212 may be transported through the density media 222 responsive to the sedimentation forces and may form a pellet 226 at an end of the structure. As the sedimentation particles (e.g. beads) are transported through the density media, the flow may wash the particles, removing unbound material and improving the detection of the assay. Moreover, the density media may be buffered with PBS which may enhance a fluorescent signal of DNA-bound dye. Sample and any unbound label may not be transported through the density media 222 and may remain within the sample or at an interface between the density media and the sample. Moreover, any red blood cells present in a whole blood sample may be less dense than the density media, and the cells may also remain at the interface between the density media and the sample.

Nucleic acid assays conducted in accordance with embodiments of the present invention may accordingly separate interfering matrix components from the nucleic acids in complexes. For example, proteins or other components with a positive or neutral charge may not form complexes with a positively-charged sedimentation particle. Other unbound particles (e.g. whole blood cells) may not travel through the density media due to the density of the particle being less than the media. Accordingly, separation may be improved. The sensitivity of detection may also be improved relative to standard techniques by the accurate separation, concentration in a pellet, and/or enhancement of the dye signal during transport through a PBS buffered density medium. Still further DNA assays in accordance with the present invention may be performed in a relatively short period of time, less than 10 minutes in some examples.

It may be of interest to directly measure cell free DNA or nucleic acid levels in whole blood samples. FIG. 3A-3B is a schematic illustration of a detection region 330 of a fluid-holding device (e.g. microfluidic device, disk) before (FIG. 3A) and after (FIG. 3B) sedimentation in accordance with an embodiment of the present invention. A whole blood sample 302 including red blood cells 305 and silica beads 315 may be introduced to the detection region 330 next to or over a density media 310. Although not shown in FIG. 3A-3B, the silica beads 315 may be modified with positively charged surface molecules such as amines to effectively bind nucleic acids in the fluid sample 302, as generally described above. The density media 310 may have a density greater than the red blood cells 305, but less than that of the silica beads 315.

Generally, blood cells may have a density less than or equal to 1.095 g/cm$^3$, and the silica beads may have a density of about 2.05 g/cm$^3$. Accordingly, the density media 310 may have a density of between about 1.095 g/cm$^3$ and 2.05 g/cm$^3$. In one example, the density media 310 has a density of 1.11 g/cm$^3$.

Sedimentation may occur under the influence of a natural gravitational field, such as by allowing the assay to sit, unpowered, under the influence of a gravitational field. Sedimentation may also occur using centrifugal force, such as by spinning a microfluidic disk. The use of a gravitational field may be preferred over a centrifugal force in embodiments where powered centrifugal force may be undesirable, such as in a circulating DNA test for first responders. For example, silica beads on the order of 10-30 microns in diameter may sediment in minutes under a normal gravitational field. Following sedimentation, as shown in FIG. 3B, the blood cells 305 may be prohibited from transport through the denser density media 310. The silica beads 315, however, may be transported through the density media 310 to a detection location, and DNA may be detected using signal from a labeling agent, as described above.

Figure 4:
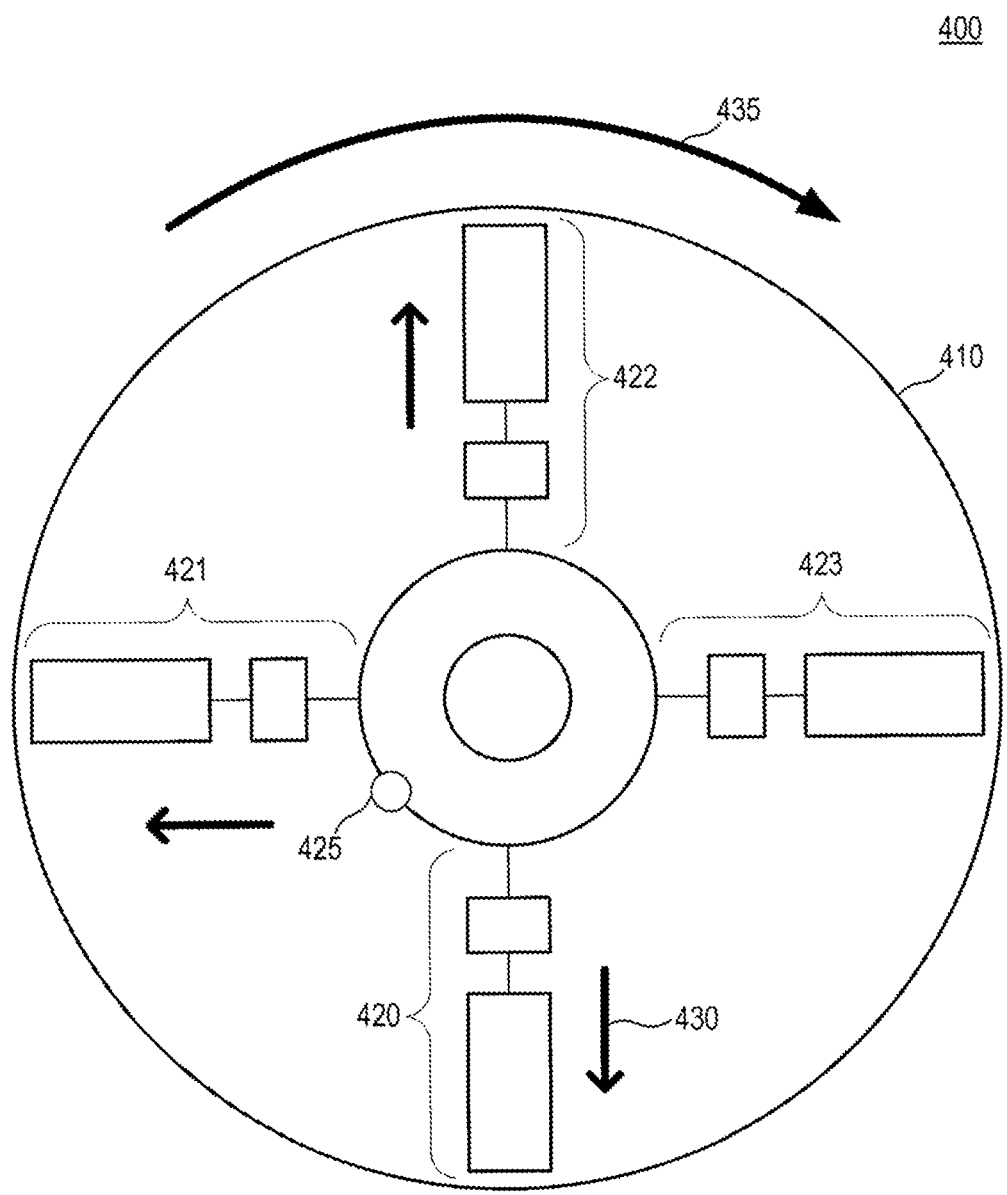
FIG. 4 is a schematic illustration of a microfluidic disk arranged in accordance with embodiments of the present invention.

In some embodiments, methods described herein may be conducted within a microfluidic disk. FIG. 4 is a schematic illustration of a microfluidic disk 400 arranged in accordance with embodiments of the present invention. The microfluidic disk 400 may include a substrate 410 which may at least partially define regions of assay areas 420, 421, 422, and 423. The microfluidic disk 400 may include a fluid inlet port 425 in fluid communication with the assay areas 420, 421, 422, and 423. Each assay area may include any of a variety of fluidic features and components, including but not limited to, channels, chambers, valves, pumps, etc. As shown in FIG. 4, each assay area includes a mixing chamber and a detection region connected by a channel containing a valve. During operation, as will be described further below, fluids including sample liquids, density media, and/or beads suspended in a fluid, may be transported using centrifugal force from an interior of the microfluidic disk 400 toward a periphery of the microfluidic disk 400 in a direction indicated by an arrow 430. The centrifugal force may be generated by rotating the microfluidic disk 400 in the direction indicated by the arrow 435, or in the opposite direction.

The substrate 410 may be implemented using any of a variety of suitable substrate materials. In some embodiments, the substrate may be a solid transparent material. Transparent plastics, quartz, glass, fused-silica, PDMS, and other transparent substrates may be desired in some embodiments to allow optical observation of sample within the channels and chambers of the disk 400. In some embodiments, however, opaque plastic, metal or semiconductor substrates may be used. In some embodiments, multiple materials may be used to implement the substrate 410. The substrate 410 may include surface treatments or other coatings, which may in some embodiments enhance compatibility with fluids placed on the substrate 410. In some embodiments surface treatments or other coatings may be provided to control fluid interaction with the substrate 410. While shown as a round disk in FIG. 4, the substrate 410 may take substantially any shape, including square.

In some embodiments, as will be described further below, the substrate 410 may itself be coupled to a motor for rotation. In some embodiments, the substrate may be mounted on another substrate or base for rotation. For example, a microfluidic chip fabricated at least partially in a substrate may be mounted on another substrate for spinning. In some examples, the microfluidic chip may be disposable while the substrate or base it is mounted on may be reusable. In some examples, the entire disc may be disposable. In some examples, a disposable cartridge including one or more microfluidic channels may be inserted into disk or other mechanical rotor that forms part of a detection system.

The substrate 410 may generally, at least partially, define a variety of fluidic features. The fluidic features may be microfluidic features. Generally, microfluidic, as used herein, refers to a system, device, or feature having a dimension of around 1 mm or less and suitable for at least partially containing a fluid. In some embodiments, 500 μm or less. In some embodiments, the microfluidic features may have a dimension of around 100 μm or less. Other dimensions may be used. The substrate 410 may define one or more fluidic features, including any number of channels, chambers, inlet/outlet ports, or other features.

Microscale fabrication techniques, generally known in the art, may be utilized to fabricate the microfluidic disk 400. The microscale fabrication techniques employed to fabricate the disk 400 may include, for example, embossing, etching, injection molding, surface treatments, photolithography, bonding and other techniques.

A fluid inlet port 425 may be provided to receive a fluid that may be analyzed using the microfluidic disk 400. The fluid inlet port 425 may have generally any configuration, and a fluid sample may enter the fluid inlet port 425 utilizing substantially any fluid transport mechanism, including pipetting, pumping, or capillary action. The fluid inlet port 425 may take substantially any shape. Generally, the fluid inlet port 425 is in fluid communication with at least one assay area 420, and may be in fluid communication with multiple assay areas 420-423 in FIG. 4. Generally, by fluid communication it is meant that a fluid may flow from one area to the other, either freely or using one or more transport forces and/or valves, and with or without flowing through intervening structures.

The assay area 420 will be described further below, and generally may include one or more channels in fluid communication with the fluid inlet port 425. Although four assay areas 420-423 are shown in FIG. 4, generally any number may be present on the microfluidic disk 400.

As the microfluidic disk 400 is rotated in the direction indicated by the arrow 435 (or in the opposite direction), a centrifugal force may be generated. The centrifugal force may generally transport fluid from the inlet port 425 into one or more of the assay areas 420-423.

Accordingly, the microfluidic disk 400 may be used to perform assays described herein. Centrifugal forces may be used to generate sedimentation forces described herein. In other examples, however, gravity may be used to generate sedimentation forces, and assays described herein may be conducted in a vial or other container.

Figures 5A, 5B, 5C:
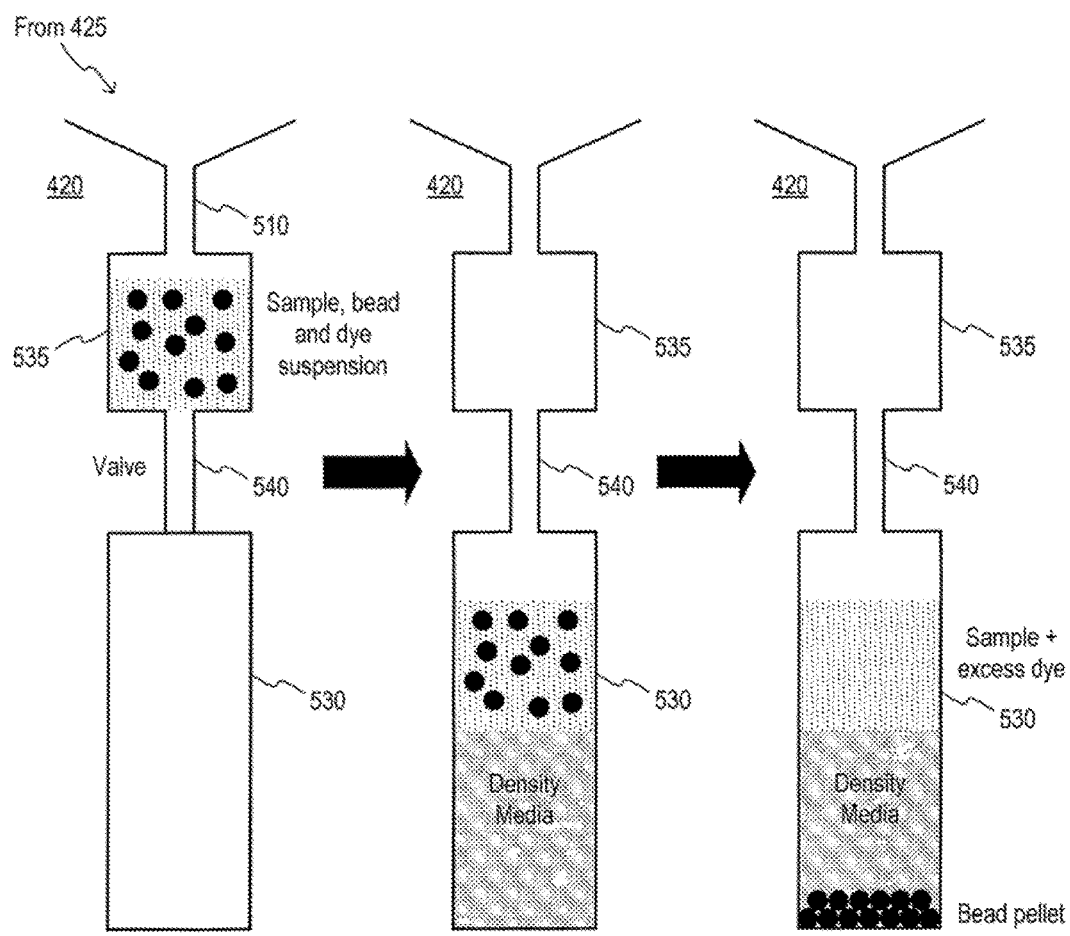
FIGS. 5A-5C are schematic illustrations of an assay area 420 of a microfluidic disk in accordance with an embodiment of the present invention.
Figure 6A:
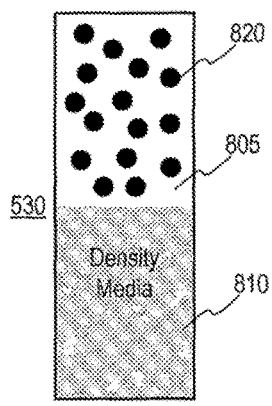
FIGS. 6A-6B, 7A-7B, and 8A-8B are schematic illustrations of a detection region containing a sample fluid and a density media in accordance with an embodiment of the present invention.

FIGS. 5A-5C are schematic illustrations of an assay area 420 of a microfluidic disk in accordance with an embodiment of the present invention. The assay area 420 includes a channel 510 in fluid communication with the fluid inlet port 425. The channel 510 may be in fluid communication with a detection region 530, which may be implemented using the detection region 330 of FIG. 3A-3B. Another reservoir 535 may be in fluid communication with the detection region 530 via a channel 540, which may include or serve as a valve. The detection region 530 may be implemented as a fluidic chamber, channel, or reservoir, and detection may occur at an end of the region. In other examples, detection may not occur in the detection region 530, but the sample may be transported elsewhere for detection.

The detection region 530 and reservoir 535 may generally be implemented using any size and shape, and may contain one or more reagents including solids and/or fluids which may interact with fluid entering and/or exiting the features.

The detection region 530 may be configured to contain a density media. Constituents of an appropriate density media are explained previously. In some embodiments, the density media may include a detergent, such as Tween® 20. The detergent may enhance a wash function of transport through the density media, as will be described further below.

Sample, sedimentation particles, and dye may first be mixed and/or incubated in the reservoir 535, as shown in FIG. 5A, then introduced at a selected time to the detection region 530 by operation of the valve 540. That is, a mixture of sample, sedimentation particles, and dye suspension may be present in the reservoir 535 (for example by introducing the different components separately, or by loading a mixture containing all components into the reservoir 535). The valve 540 may be closed to contain the components in the reservoir 535 and allow the components to incubate to form complexes.

On opening the valve 540, as shown in FIG. 5B, the mixture including the sample, beads, and dye, which may have formed complexes, may be introduced to the detection region 530. In some examples, the reservoir 535 may not be provided, and the mixture may be loaded directly into the detection region 530, which may be a channel or chamber. Detection may take place at an end of the detection region 530. The detection region 530 may further have a tapered or other shape at the end of the detection region 530, as was shown in FIG. 3A-3B.

The detection region 530 may be a channel or chamber and may vary in configuration in accordance with the detection technique employed, as will be described further below. The detection region 530 may generally be configured to allow for detection of a signal emitted by labeling agents in a complex. The complex may include cell-free DNA and labeling agent in embodiments pertaining to cell-free DNA assays. The complexes include sedimentation particles (e.g. beads).

Centrifugal forces may generally be used to transport the mixture from the inlet port 425 toward the detection region 530. Additionally, centrifugal forces may be used to transport density media from the reservoir 535 to the detection region 530. In other examples, pressure-driven or other flow drivers may be used to load fluids into the device and transport the mixture to the detection region 530.

Incubation of sedimentation particles and labeling agents with the sample may take place within a microfluidic disk. Referring again to FIG. 5A, a fluid sample containing a target analyte may be introduced to the inlet port 425 and provided to the reservoir 535 through the channel 510. Any of a variety of suitable fluid samples may be used including, but not limited to, whole blood, buffer solutions, serum, or other biological fluid samples. Generally, the fluid sample will include target analytes to be detected in accordance with embodiments of the present invention. The fluid sample may contain beads designed to bind to nucleic acids and/or label agents designed to bind nucleic acids. In other examples, the beads and/or label agents may be introduced to the fluid sample within the microfluidic disk 400. For example, a fluid containing the beads and/or label agents may be provided to a different inlet port in fluid communication with the channel 510 of FIG. 5A-5C. Either by mixing components or by providing a fluid containing the components, a sample fluid including beads, target analytes, and labeling agents, may be transported to the detection region 530 of FIG. 5A-5C. The transport of the sample fluid may occur through any type of transport mechanism, including centrifugal force, pressure-driven flow, pumping, or other mechanisms. In other examples, beads having capture agents on their surface may be incubated with target analyte and/or labeling agents prior to introduction to a microfluidic disk. In such an example, complexes may be formed on beads in a sample fluid prior to providing the sample fluid to the microfluidic disk.

The detection region 530 of FIG. 5A-5C may contain density media, or density media may be transported into the detection region 530 from another location, such as from the reservoir 535. The channel 540 may have a width selected to serve as a valve, such that a spin rate over a threshold amount is required to initiate a flow of the density media from the reservoir 535 through the channel 540. In some examples, the channel 540 has a width selected such that any spin rates used to transport sample into the reservoir 535 is insufficient to transport the sample into the detection region 530. A spin rate of the microfluidic disk 400 may then be increased to initiate or enhance a flow of the sample from the reservoir 535 into the detection region 530. In this manner, the channel 540 may function as a valve. Other valve structures such as wax plugs that melt at a known temperature may be used in other examples.

Once the mixture of sample, bead, and dye is in the detection region 530 above the density media, sedimentation forces may be used to transport the beads through the density media to form a bead pellet, as shown in FIG. 5C. If dye and target analytes are present on the bead, they may be detected in the concentrated pellet.

Accordingly, a sample fluid including: 1) beads; 2) target analytes; and 3) labeling agents may be transported to an interface with a density media and sedimentation forces used to transport the beads, along with any bound complexes, through the density media to form a pellet at the end of the detection region.

Figure 6B:
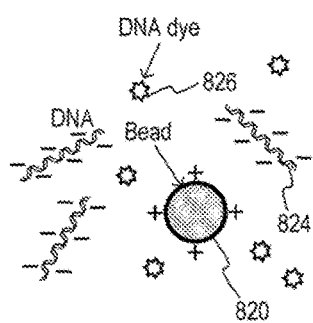

FIGS. 6A-6B, 7A-7B, and 8A-8B are schematic illustrations of the detection region 530 containing a sample fluid 805 and a density media 810 in accordance with an embodiment of the present invention. Components of the sample fluid 805 are shown for purposes of illustration beneath the detection region 530 in FIG. 8B. Schematic views of the sample components, and complex formation (FIGS. 6B, 7B, and 8B) are shown below the detection region view (FIGS. 6A, 7A, and 8A) for ease of illustration. The sample fluid includes plurality of beads, including a bead 820 with positive surface charge. The sample fluid 805 further includes target analytes, such as DNA 824, and labeling agents 826 (FIG. 6B).

Figure 7A:
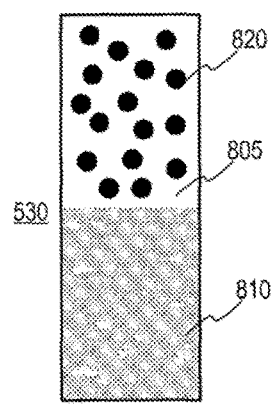
Figure 7B:
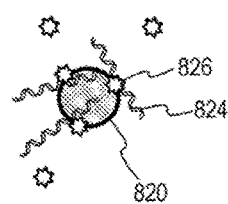
Figure 8B:
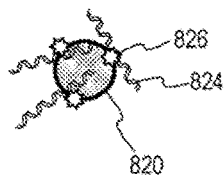

The sample fluid may then be incubated. FIG. 7A is a schematic illustration of the detection region 530 containing the sample fluid 805 and the density media 810 following an incubation period. Complexes have formed on the bead 820. The target analyte 824 has bound to the bead 820 and labeling agent 826 (FIG. 7B). Some unbound, free labeling agents, however, remain in the sample fluid 805. A time of little to no centrifugal force may be provided to allow for incubation. Additionally, in some examples, a region of the microfluidic disk containing the sample fluid may be heated to enhance incubation. In this manner, complexes may be formed on the beads. As understood in the art, the amount of labeling agent bound to complexes on the beads will generally be proportional to the amount of target analyte in the fluid sample. Any number of complexes may be formed on the beads, with three complexes shown on the bead 820 in FIG. 7B.

Figure 8A:
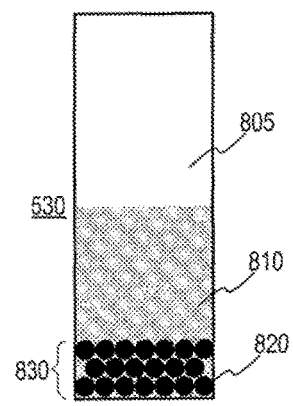

The beads may then be transported through the density media. The beads are transported through the density media using centrifugal force, such as that which may be applied by a motor, described further below. Following a period of centrifugal force, the beads may be concentrated in a detection location. FIG. 8A is a schematic illustration of the detection region 530 following transport of beads through the density media. The sample fluid 805 may remain separated from the density media 810, as the density media 810 may have a density higher than that of the sample fluid 805. Free, unbound labeling agent, may remain in the sample fluid 805. Beads 820, including complexes, may be transported through the density media 810 to a detection location 830. Beads at the detection location 830 are shown for purposes of illustration under the detection region 530 in FIG. 8B. The bead 820 includes complexes containing target analyte 824 and labeling agent 826. However, unbound labeling agent may not be found in the detection location 830. As shown in FIGS. 6A-6B, 7A-7B, and 8A-8B, centrifugal force may accordingly be used to separate complexed beads from a sample fluid and to concentrate the complexed beads. In this manner, the need for additional wash and amplification steps in a nucleic acid quantification assay may be reduced or eliminated. Signal from labeling agent of the concentrated beads may be detected from the detection location 830 using, for example, the detection module examples described below.

Figure 9:
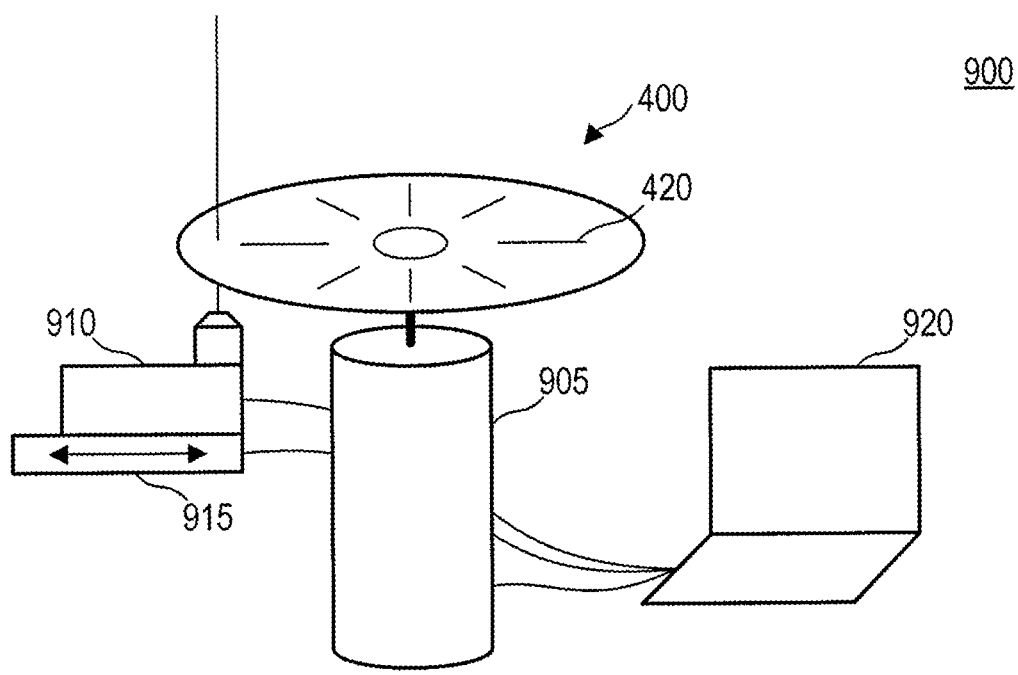
FIG. 9 is a schematic illustration of a system according to an embodiment of the present invention.

FIG. 9 is a schematic illustration of a system according to an embodiment of the present invention. The system 900 may include the disk 400 of FIG. 4 with one or more assay areas 420. A motor 905 may be coupled to the disk 400 and configured to spin the disk 400, generating centrifugal forces. A detection module 910 may be positioned to detect signal from labeling agents in a detection region of the assay area 420, as will be described further below. An actuator 915 may be coupled to the detection module 910 and configured to move the detection module along the detection region in some examples. A processing device 920 may be coupled to the motor 905, the detection module 910, and/or the actuator 915 and may provide control signals to those components. The processing device 920 may further receive electronic signals from the detection module 910 corresponding to the labeling agent signals received by the detection module 910. All or selected components shown in FIG. 9 may be housed in a common housing in some examples. Microfluidic disks, which may be disposable, may be placed on the motor 905 and removed, such that multiple disks may be analyzed by the system 900.

The motor 905 may be implemented using a centrifugation and/or stepper motor. The motor 905 may be positioned relative to the detection module 910 such that, when the disk 400 is situated on the motor 905, the disk is positioned such that a detection region of the assay area 420 is exposed to the detection module 910.

The detection module 910 may include a detector suitable for detecting signal from labeling agents in complexes that may include labeling agent. In nucleic acid (e.g. cell-free DNA) assays, the complexes may include DNA and labeling agent. The complexes may be formed on the surface of one or more sedimentation particles (e.g. beads), as described further below. The detector may include, for example, a laser and optics suitable for optical detection of fluorescence from fluorescent labeling agents. The detection module may include one or more photomultiplier tubes. In other examples, other detectors, such as photodiodes or CCD cameras, may be used. The actuator 915 may move the detector in some examples where signal may be detected from a variety of locations of the microfluidic disk 400, as will be described further below.

The processing device 920 may include one or more processing units, such as one or more processors. In some examples, the processing device 920 may include a controller, logic circuitry, and/or software for performing functionalities described herein. The processing device 920 may be coupled to one or more memories, input devices, and/or output devices including, but not limited to, disk drives, keyboards, mice, and displays. The processing device may provide control signals to the motor 905 to rotate the disk 400 at selected speeds for selected times, as will be described further below. The processing device may provide control signals to the detection module 910, including one or more detectors and/or actuators, to detect signals from the label moieties and/or move the detector to particular locations, as will be described further below. The processing device may develop these control signals in accordance with input from an operator and/or in accordance with software including instructions encoded in one or more memories, where the instructions, when executed by one or more processing units, may cause the processing device to output a predetermined sequence of control signals. The processing device 920 may receive electronic signals from the detection module 910 indicative of the detected signal from labeling agents. The processing device 920 may detect a target analyte and/or calculate a quantity of a target analyte in a fluid sample based on the signals received from the detection module 910, as will be described further below. Accordingly, the processing device 920 may perform calculations as will be described further below. The calculations may be performed in accordance with software including one or more executable instructions stored on a memory causing the processing device to perform the calculations. Results may be stored in memory, communicated over a network, and/or displayed. It is to be understood that the configuration of the processing device 920 and related components is quite flexible, and any of a variety of computing systems may be used including server systems, desktops, laptops, controllers, and the like.

Having described examples of microfluidic disks and systems in accordance with embodiments of the present invention, methods for conducting assays will now be described. Some discussion will also be provided regarding mechanisms for sedimentation and centrifugation. The discussion regarding mechanisms is provided as an aid to understanding examples of the present invention, but is in no way intended to limit embodiments of the present invention. That is, embodiments of the present invention may not employ the described mechanisms.

Sedimentation of spheres may occur within a viscous fluid under the influence of a gravitational field (which may be natural or induced by centrifugation). The settling velocity of approximately spherical particles may be described by Stoke's flow equations:

$$V_s = \frac{2}{9} \frac{(\rho_p - \rho_f)}{\mu} g R^2;$$

where $V_s$ is the sedimentation velocity, $\mu$ is the fluid viscosity, $\rho_p$ is the density of the particle, $\rho_f$ is the density of the fluid, $g$ is acceleration due to effective gravity, and $R$ is the particle radius. Note that sedimentation rate scales with the square of particle radius and therefore a small difference in radius may form a basis for separation of particles in some examples, as they may sediment at a different rate. There is also a linear dependence of sedimentation rate with the difference in density between the particle and the surrounding fluid, which may also be an effective mechanism for separation. Accordingly, beads or other particles may be separated according to their density and/or radius based on different sedimentation velocities. Separation of particles using these principles may be referred to as "rate zonal centrifugation."

For nanometer scale particles, such as nucleic acids, gravitational forces may act in conjunction with Brownian diffusion, but neither will generally cause motion of these nanometer scale particles over significant distances during typical centrifugal conditions (<100,000 g). Accordingly, beads with affinity for nucleic acids may be used to separate nucleic acids from a fluid sample containing mixture of other small molecules. By capturing nucleic acids on the bead surface, and separating the beads from the remaining sample using sedimentation (e.g. centrifugal or gravitational) forces, the need for wash steps may be reduced or eliminated, because unbound labeling agents and/or other molecules may be dissociated from the beads by fluid flow.

Example 1 mL of binding buffer (1M $Na_2SO_4$, 1M $NaCH_3CO_2$, pH 3) may be added to 50 mg of 1 μm amine-modified silica microparticles. The substances may be mixed by vortexing, pipeting, and sonication to achieve a uniform suspension of particles. 1 μL of 2000×SYBR® Gold may be added to result in a particle suspension for use in a DNA assay. The mixture may be incubated with a sample for 10 minutes at room temperature protected from light with mixing. 4 μL of the suspension may be added to a channel preloaded with 3.5 μL of Percoll®. The channel may be spun at 8000 rpm for 45 s, transporting the microparticles through the Percoll® to form a pellet in a detection area. The pellet may be imaged using a fluorescent microscope with excitation 485 nm and emission 535 nm.

Figure 10:
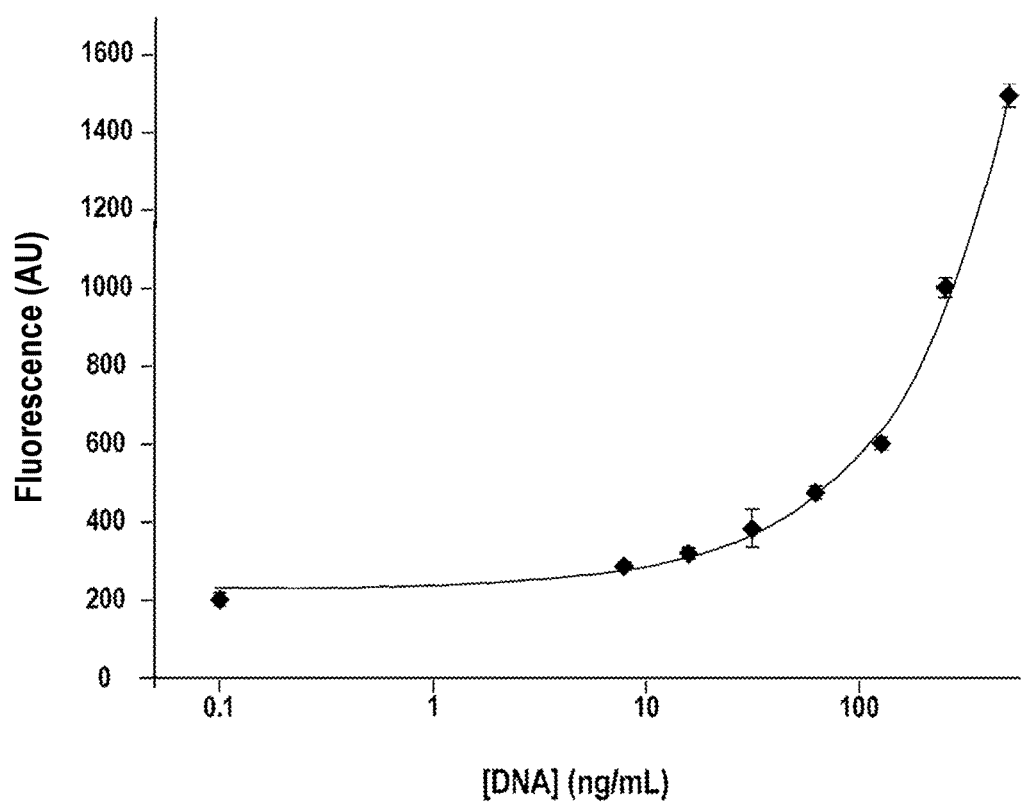
FIG. 10 shows a dose response curve generated using serial dilutions of DNA.

The sample may have 2 μL of serum. FIG. 10 shows a dose response curve generated using serial dilutions of DNA. A limit of detection was calculated to be 1.1 ng/mL, and a limit of quantitation was calculated to be 36.5 ng/mL. The normal range of cell-free DNA in health samples may be between 65-877 ng/mL, accordingly, these detection and quantitation limits are within a range useful for clinical significance. Capture efficiency was found to be greater than 99 percent in some examples. 1000 ng was spiked into 1 mL of sample and captured using amino-modified silica microparticles. After 10 minutes, SYBR® gold was added and the microparticles sedimented. Approximately 3.4 ng remained unbound to the particles.

From the foregoing it will be appreciated that, although specific embodiments of the invention have been described herein for purposes of illustration, various modifications may be made without deviating from the spirit and scope of the invention.

What is claimed is:

1. A method of conducting an assay, the method comprising:
    generating complexes which bind to a plurality of beads in a fluid sample, individual ones of the complexes comprising a negatively-charged target analyte bound, using a charge, directly to a positively charged surface of the bead, and a labeling agent bound to the target analyte, wherein the generating occurs in the presence of a binding buffer configured to provide an acidic pH to maintain the negative charge of the target analyte;
    transporting the plurality of beads including the complexes through a density media, wherein the density media has a density less than a density of the beads and greater than a density of the fluid sample, and wherein the transporting occurs, at least in part, by a sedimentation force; and
    detecting a signal from the labeling agents of the complexes.

2. The method of claim 1, wherein the target analyte includes a nucleic acid.

3. The method of claim 2, wherein the labeling agent comprises a nucleic acid dye.

4. The method of claim 3 wherein the nucleic acid dye has a binding constant <20 nM.

5. The method of claim 3, wherein the beads have a positively-charged surface in the fluid sample and the nucleic acid has a negative charge.

6. The method of claim 5, wherein the fluid sample includes kosmotropes or order-forming salts.

7. The method of claim 5, wherein the fluid sample has an acidic pH<4 in order to cause contaminating proteins to exhibit positive charge.

8. The method of claim 3, wherein the fluid sample includes chaotropic salts.

9. The method of claim 1, wherein said fluid sample comprises whole blood, wherein the density media has a density greater than a density of red blood cells, and wherein the method further comprises:
    separating the red blood cells from the plurality of beads at least in part by applying a sedimentation force to the fluid sample such that the red blood cells remain at an interface between the density media and the fluid sample.

10. The method of claim 1, wherein a surface of the beads comprises amines.

11. The method of claim 1, wherein the density media comprises a detergent.

12. The method of claim 2, wherein the nucleic acid is a cell-free DNA.

13. The method of claim 1, wherein the sedimentation force comprises a centrifugal force.

14. The method of claim 1, wherein the transporting forms a pellet.

15. The method of claim 1, wherein the density media comprises sucrose, dextran, or a buffered density media.

16. The method of claim 1, wherein the binding buffer comprises a high salt concentration and a low pH.

17. The method of claim 1, wherein the acidic pH is less than 4.

18. A method of conducting an assay, the method comprising:
    generating complexes which bind to a plurality of beads in a fluid sample, individual ones of the complexes comprising a negatively-charged target analyte bound, using a charge, directly to a positively charged surface of the bead, and a labeling agent bound to the target analyte, wherein the generating occurs in the presence of a binding buffer configured to provide an acidic pH to maintain the negative charge of the target analyte and a high salt concentration;
    transporting the plurality of beads including the complexes through a density media, wherein the density media has a density less than a density of the beads and greater than a density of the fluid sample, and wherein the transporting occurs, at least in part, by a sedimentation force; and
    detecting a signal from the labeling agents of the complexes.

* * * * *